United States Patent [19]

Yaku et al.

[11] Patent Number: 4,970,150

[45] Date of Patent: Nov. 13, 1990

[54] PROCESS FOR PREPARING CHITOSAN OLIGOSACCHARIDES

[75] Inventors: Fumiko Yaku, Suita; Ryutarou Tanaka; Einosuke Muraki, both of Osaka; Shizu Fujishima; Masaru Miya, both of Ikeda, all of Japan

[73] Assignee: Agency of Industrial Science & Technology, Tokyo, Japan

[21] Appl. No.: 363,802

[22] Filed: Jun. 9, 1989

[30] Foreign Application Priority Data

Jul. 6, 1988 [JP] Japan ................... 63-169392

[51] Int. Cl.$^5$ ............... C12P 19/04; C12N 9/42; C07H 1/00
[52] U.S. Cl. ................. 435/101; 435/209; 435/99; 435/917; 435/945; 536/55.1; 536/55.2; 536/20
[58] Field of Search ............. 435/99, 209, 945, 917; 536/55.1, 55.2, 20

[56] References Cited

U.S. PATENT DOCUMENTS

| | | | |
|---|---|---|---|
| 3,310,476 | 3/1967 | Yerkes | 435/209 |
| 3,677,899 | 7/1972 | Kawai et al. | 435/209 |
| 4,089,746 | 5/1978 | Masri et al. | 435/99 |
| 4,148,689 | 4/1979 | Hino et al. | 435/182 |
| 4,167,447 | 9/1979 | Masri et al. | 435/178 |
| 4,579,942 | 4/1986 | Brode et al. | 536/84 |
| 4,746,611 | 5/1988 | Fujishima et al. | 435/209 |

FOREIGN PATENT DOCUMENTS 280277 of 1985 Japan ................... 435/209

OTHER PUBLICATIONS

J. Am. Chem. Soc., 79, 5046–5049 (1957).
Methods of Carbohydrate Chemistry, I., pp. 305–308 (1962); Academic Press, N.Y.

*Primary Examiner*—Ronald W. Griffin
*Assistant Examiner*—Pamela S. Webber
*Attorney, Agent, or Firm*—Armstrong, Nikaido, Marmelstein, Kubovcik & Murray

[57] ABSTRACT

A process for preparing a low-molecular weight chitosan which comprises adding chitosan to water containing a monobasic acid to prepare an intimate chitosan-water mixture and treating said mixture with cellulase.

2 Claims, No Drawings

PROCESS FOR PREPARING CHITOSAN OLIGOSACCHARIDES

BACKGROUND OF THE INVENTION

The present invention relates to a process for preparing a low-molecular weight chitosan from a high-molecular weight chitosan.

A chitosan is a basic polysaccharide comprising 2-amino-2-deoxy-D-glucoses bonded to each other through $\beta$-1,4 glycoside linkages and usually prepared by deacetylating natural chitin. Since the chitosan is basic, it is soluble in an aqueous dilute acid solution. However, since the chitosan is a polymeric compound having a molecular weight of several hundreds of thousands, e.g., a 0.2 % chitosan solution prepared by dissolving chitosan in a solution of 0.8 % sodium acetate in 1.2 % acetic acid has a viscosity ($\eta sp/c$) as high as 9 to 16, which makes it very difficult to prepare a chitosan solution having a high concentration.

If it is possible to reduce the molecular weight of the chitosan, a chitosan solution having a high concentration and a low viscosity can be advantageously used in the field of fine chemicals such as pharmaceuticals and cosmetics.

A glucosamine oligosaccharide prepared by reducing the molecular weight of the chitosan has been recognized to have various antibacterial properties and attracted attention as a less toxic antibacterial agent.

Therefore, if the molecular weight of the chitosan can be reduced to a desired range depending upon its application, the chitosan can be further effectively utilized. For this reason, the establishment of a technique for reducing the molecular weight has been eagerly desired in various fields. The following methods (1) to (4) are known in the art for preparing a low-molecular weight chitosan:

(1) a method wherein the glycoside linkages of chitin as a raw material are cleaved to reduce the molecular weight when chitin is deacetylated through alkali treatment.

(2) a method wherein deacetylation is conducted after chitin as a raw material is treated with a dilute acid to cleave glycoside linkages.

(3) a method wherein chitosan is treated with an aqueous hydrogen peroxide solution of an aqueous peroboric acid solution.

(4) a method wherein chitosan is treated with a chlorine gas.

However, in the above-described methods (1) and (2), not only it is necessary to employ severe conditions of heating at 100° C. for 5 to 24 hr but also it is very difficult to prepare chitosan having an arbitrarily reduced molecular weight. Further, since there occurs a side reaction, the resultant chitosan is colored, which renders the chitosan unfavorable for use as a raw material for the above-described fine chemicals.

In the method (3), the glycoside linkages can be cleaved without accompanied by deamination. However, the low-molecular chitosan prepared by this method has a molecular weight of about 10,000 at the lowest and therefore cannot be dissolved in neutral water.

In the method (4), not only a toxic gas must be used but also a colored substance is formed in some cases.

The present invention has been made with a view to eliminating the drawbacks accompanying the above-described conventional methods and based on a finding that cellulase, i.e., a cellulolytic enzyme, invariably has a chitosan decomposing activity, i.e., a chitosanase activity.

SUMMARY OF THE INVENTION

A first object of the present invention is to provide a process for preparing a low-molecular weight chitosan under mild reaction conditions with simple operation.

A second object of the present invention is to provide a process for preparing a low-molecular weight chitosan having a molecular weight suitable for desired application.

DESCRIPTION OF THE PREFERRED EMBODIMENTS

The process for preparing a low-molecular weight chitosan according to the present invention comprises dissolving a chitosan in water containing a monobasic acid to prepare an intimate chitosan-water mixture and treating the mixture with cellulase.

The chitosan used in the present invention may be one prepared by any method. For example, as known in the art, it is possible to use a chitosan prepared by treating natural chitin prepared by removing calcium and protein from a crab shell or a lobster shell with a deacetylating agent such as a 47% sodium hydroxide solution. The deacetylation is conducted by placing 100 g of purified chitin in a nickel vessel, adding 1700 g of an aqueous 47% sodium hydroxide solution to the chitin, heating the mixture at 110° C. or 60° C. for 1 to 2 hr under a nitrogen gas flow. The reaction product is separated from the alkaline solution, placed in hot water of about 80° C. for 1 hr, and washed with water to a neutral state, thereby preparing a chitosan having a degree of deacetylation of 80%. Further, the alkali treatment and washing with water are repeated at least twice to prepare a chitosan having a degree of deacetylation of 90 to 95%.

In the present invention, the chitosan is first dissolved in water containing a monobasic acid to prepare an intimate chitosan-water mixture.

Examples of the monobasic acid include hydrochloric, acetic, formic, nitric and lactic acids. The water containing a monobasic acid is an aqueous solution having a monobasic acid concentration of 0.2 to 5% by weight, preferably 0.5 to 3% by weight, or a buffer solution of the above-described monobasic acid, e.g., an acetic acid-sodium acetate buffer solution or a lactic acid-sodium lactate buffer solution.

The monobasic acid concentration of each of the above-described buffer solutions is in the same range as that described above.

The pH value of the intimate chitosan-water mixture in the present invention is 4.0 to 7.5, preferably 4.5 to 7.0. When the pH value is 4.0 to 6.0, a transparent solution of chitosan is obtained, while when the pH value is about 7.0, a gel-like dispersion is obtained. Both the transparent solution and the dispersion may be used in the present invention. The pH value range of 4.0 to 7.5 corresponds to a pH value range where the cellulase exhibits a chitosanase activity. When the pH value is less than 4.0 or exceeds 7.5, it is impossible to reduce the molecular weight of the chitosan through the use of cellulase.

According to the present invention, cellulase is then added to the aqueous dilute acid solution or gel-like dispersion of chitosan adjusted so as to be in the above-described pH range in an amount of about 1/5 to 1/100 of the weight of the chitosan when the cellulase is solid and about 10 to 100 units in terms of avicelase activity per gram of the chitosan when the cellulase is liquid. The mixture is allowed to stand or shaken at a temperature of 10° to 70° C., preferably 20° to 60° C. for several tens of minutes to several tens of hours.

This brings about a rapid lowering in the viscosity in the case of the aqueous dilute acid solution of chitosan and a rapid dissolution in the case of the gel-like dispersion of chitosan, thereby giving a transparent, lowly viscous solution.

It is possible to prepare various low molecular weight chitosans ranging from one comprising a dimer having a relatively low molecular weight of 360 to one having a relatively high molecular weight of several tens of thousands depending upon the amount of addition of cellulase.

The low-molecular weight chitosans are separated from the reaction mixture as follows. An aqueous sodium hydroxide solution is added to the reaction mixture to alkalize the reaction mixture. This causes precipitation of low-molecular weight chitosans comprising a decamer and higher oligomers. Since oligosaccharides comprising oligomers lower than the decamer remain dissolved in the solution both of them are separated from each other by centrifugation. The low-molecular weight chitosans comprising a decamer and higher oligomers are redissolved in 0.1N-hydrochloric acid or sulfuric acid and mixed with ethanol to conduct fractional precipitation into fractions according to the molecular weight. The filtrate containing the chitosans comprising oligomers lower than the decamer obtained in the centrifugation can be fractionated into the oligomers from dimer to the decamer depending upon the molecular weight by various chromatographic methods.

In the present invention, in order to prepare an oligosaccharide having a relatively low molecular weight, the amount of addition of the cellulase is increased within the above-described range to complete the reaction in several hours, or the amount of the cellulase is reduced to prolong the reaction time.

On the other hand, in order to prepare a relatively high-molecular weight chitosan subjected to the molecular weight reduction, it is suitable to reduce the amount of the enzyme to thereby complete the reaction in a short time.

The cellulase used in the present invention may be commercially available one, a crude cellulase preparation extracted from an animal or vegetable tissue, a culture per se of cellulolytic fungi, or purified preparations thereof. Specific examples of the cellulase include those produced by the fungi belonging to the genus Trichoderma or Aspergillus, those extracted from a termite, and preparations having a cellulase activity. In the present invention, these enzymes may be used alone or in a combination of two or more of them different from each other in the origin. Further, it is also possible to use extracts or cell cultures containing these enzymes as the enzyme source.

Generally the cellulase is believed to be a composite enzyme system composed of a component having an exoglucanase activity (avicelase activity), one having an endoglucanase activity (carboxymethylcellulase), and one having a β-glucosidase activity.

Although the cellulase sometimes exhibits a hemicellulase activity or a chitinase activity besides these types of activity, it is not known to date that the cellulase has a chitosanase activity as well.

The present invention has been made based on the finding that a chitosanase activity as high as about 1/5 of an avicelase activity exists in any type of cellulase. The reason why the cellulase has a chitosanase activity is believed to beside in that there is a high possibility that chitosan exists in the cell wall besides cellulose and the cells simultaneously produce the cellulase and the chitosanase because of necessity of simultaneously decomposing the cellulose and the chitosan.

As regards the animal and vegetable cellulases, cellulose and chitosan naturally occur simultaneously in many cases, and the cellulase is believed to be invariably endowed with a chitosanase activity.

As described above, the present invention relates to a process for enzymaticallt decomposing chitosan by utilizing the chitosanase activity of the cellulase. Therefore, the process of the present invention makes it possible to bring about only the intended cleavage of the glycoside linkages without causing occurrence of a side reaction at a temperature near room temperature and a pH value near neutrality, so that a low-molecular weight chitosan can be prepared in a high yield without being accompanied by the elimination of an amino group or formation of a colored substance.

The present invention will now be described with reference to the following Examples.

EXAMPLE 1

90 ml of an acetate buffer having a pH value of 4.0 was added to 1 g of chitosan prepared by deacetylating natural chitin to dissolve the chitosan. The resultant solution had a pH value of 4.5.

To this solution was added 10 ml (100 units based on chitosan) of a 1% solution of commercially available cellulase produced by *Trichoderma viride* (cellulase-Onozuka R-10). The mixture was shaken at 40° C. for 24 hr to obtain a chitosan mixture comprising the dimer to the octamer. After neutralization, the cellulase and inorganic substances were removed by gel filtration, and solidification was conducted to obtain a chitosan mixture comprising the dimerr to the octamer in a yield of 85%. The average molecular weight was 980.

EXAMPLE 2

10 g of chitosan prepared be deacetylating natural chitin to a degree of 95% was dissolved in 450 ml of 0.12M acetic acid, and a 1M aqueous sodium hydroxide solution was added to adjust the pH value to 5.0. Separately, cellulase produced by *Aspergillus niger* (Cellulosin AP) was subjected to ultrafiltration to remove fractions having a molecular weight of 10,000 or less, thereby giving purified Cellulosin AP. This purification increased the avicelase activity by a factor of 2. 50 ml of a 2% solution of the purified Cellulosin AP (1000 units based on chitosan) was added to the above-described chitosan, and the mixture was shaken at 50° C. for 3 hr. When the pH value of the reaction solution was adjusted to 8 to 9, a white powdery precipitate was formed. The precipitate was centrifuged, washed with water, and dried to give a relatively high-molecular weight chitosan subjected to molecular weight reduction. The yield and average molecular weight were 72% and 11,000, respectively.

EXAMPLE 3

An extract prepared by subjecting ergates of Formosan white ant to ultrasonic treatment in a 0.05M acetate buffer (pH 4.6) was fractionated with ammonium sulfate to prepare crude cellulase from 50 to 65% saturation fractions. The avicelase activity of the cellulase was 1.4 units/mg.

1.5 g of chitosan which has been deacetylated to a degree of 99% was swollen with water and dissolved in 30 ml of 0.5M lactic acid. Water was added to the solution to a total amount of 60 ml. The pH value of this solution was 5.4. 70 mg (70 unit based on chitosan) of cellulase of the Formosan white ant was added to the chitosan solution and allowed to stand at room temperature for 48 hr. In this case, the viscosity was decreased to 1/10 of the original one. Powder of a low-molecular weight chitosan was prepared in the same manner as that of Example 2.

The yield and average molecular weight were 56% and 6,800, respectively.

EXAMPLE 4

100 g of chitosan was dissolved in 800 ml of 0.1M acetic acid, and 1M sodium hydroxide was added thereto to adjust the pH value to 7.2, thereby giving a gel-like chitosan dispersion. 50 ml of commercially available Genencor-Cellulase 150L (avicelase activity: 115 units/ml) was added to the dispersion, and the mixture was shaken at 70° C. for 30 min. This caused the gel-like chitosan to be dissolved, thereby giving a transparent solution. This solution as fractionated with a column for liquid chromatogracy. As a result, it was found that oligosaccharides were contained therein in the following proportions: 19% of chitobiose; 28% of chitotriose; 23 of chitotetraose; 7% of chitopentaose; 6% of chitohexaose; 5% of chitoheptaose to chitononaose; and 12% or more of chitodecaose.

EXAMPLE 5

100 ml of a water-soluble nutrient medium containing a suitable amount of cellulose powder added thereto as a carbon source was placed in a 500-cc flask sterilized. *Trichoderma viride* QM414 was inoculated thereon and incubated at 30° C. under aerobic conditions for 10 days. The pH value of the culture solution was kept constant at 5.4.

Separately, 200 ml of a 1% chitosan solution having a pH value of 6.0 was prepared. 50 ml of the above-described culture solution (enzyme content: 120 mg) was added thereto, and the mixture was shaken at room temperature (15° to 20° C.) for 3 hr. A 1M aqueous sodium hydroxide solution was added to adjust the pH to 8 to 9, thereby forming a white precipitate. The content of the low-molecular weight chitosan contained in the supernatant was measured by the indole method and found to be 14.4%, and the chitosan consisted of 5.3 monomer units on the average. The precipitate was treated in the same manner as that of Example 2 to give a powdery low-molecular weight chitosan in a yield of 74%. The average molecular weight was 3,200.

What is claimed is:

1. A process for the preparation of low molecular weight chitosan oligosaccharides, which comprises:
    (a) preparing a chitosan-water mixture having a pH of 4.0 to 7.5 from native chitosan and water containing a monobasic acid;
    (b) adding to the resulting aqueous mixture 1 to 20% by weight of a solid cellulase or a liquid cellulase having an avicelase activity of 10 to 100 units per gram of chitosan, said cellulase being selected from the group consisting of cellulase produced by *Trichoderma viride*, cellulase extracted from the Formosan white ant and cellulase produced by *Aspergillus niger*, and reacting the native chitosan and the cellulase at a temperature of 10° to 70° C.;
    (c) adding an alkali to the resulting reaction mixture to precipitate low-molecular weight chitosan oligomers more highly polymeric than the decamer; and
    (d) separating the precipitate of low-molecular weight chitosan oligomers more highly polymeric than the decamer from the reaction mixture.

2. A process according to claim 1, comprising the additional step, after separating the said precipitate, of recovering chitosan oligomers less polymeric than the decamer from the reaction mixture.

* * * * *